(12) United States Patent
Fantuzzi

(10) Patent No.: US 12,350,445 B2
(45) Date of Patent: Jul. 8, 2025

(54) DUAL HUB INTRODUCER SHEATH

(71) Applicant: ABIOMED, Inc., Danvers, MA (US)

(72) Inventor: Glen R. Fantuzzi, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 264 days.

(21) Appl. No.: 16/815,690

(22) Filed: Mar. 11, 2020

(65) Prior Publication Data

US 2020/0289794 A1    Sep. 17, 2020

Related U.S. Application Data

(60) Provisional application No. 62/817,901, filed on Mar. 13, 2019.

(51) Int. Cl.
*A61M 25/00* (2006.01)
*A61M 1/00* (2006.01)
(Continued)

(52) U.S. Cl.
CPC ...... *A61M 25/0097* (2013.01); *A61M 1/3613* (2014.02); *A61M 1/3659* (2014.02);
(Continued)

(58) Field of Classification Search
CPC ...... A61M 2039/0686; A61M 25/0097; A61M 25/0668; A61M 2025/09125
See application file for complete search history.

(56) References Cited

U.S. PATENT DOCUMENTS 5,254,097 A * 10/1993 Schock ............... A61M 39/04
604/167.04
5,295,969 A * 3/1994 Fischell ............ A61M 39/0606
604/168.01
(Continued)

FOREIGN PATENT DOCUMENTS

CN   108577937 A   9/2018
JP   H0999091 A    4/1997
(Continued)

OTHER PUBLICATIONS

Esposito, M. L., et al., ""Left Ventricular Unloading Before Reperfusion Promotes Functional Recovery After Acute Myocardial Infarction"", Journal of the American College of Cardiology, Elsevier, vol. 72, No. 5, May 2018.
(Continued)

*Primary Examiner* — William R Carpenter
(74) *Attorney, Agent, or Firm* — Botos Churchill IP Law LLP

(57) ABSTRACT

There is provided an introducer system for percutaneously delivering a first and a second medical device to a patient. The system may comprise an introducer sheath having a longitudinal axis and a lumen formed therein. The system may also comprise a hub coupled to a proximal end of the sheath. The hub may comprise a first arm having a first lumen and a first hemostasis valve for the passage of the first medical device. The hub may also comprise a second arm coupled to the first arm and having a second lumen and a second hemostasis valve for the passage of the second medical device. Further, the hub may comprise a connection port such that the first lumen and the second lumen are in communication with the lumen of the introducer sheath for the passage of at least one of the first and second medical devices through the introducer sheath for delivery to the patient.

27 Claims, 7 Drawing Sheets

(51) Int. Cl.
*A61M 1/36* (2006.01)
*A61M 25/06* (2006.01)
*A61M 39/02* (2006.01)
*A61M 39/06* (2006.01)
*A61M 60/113* (2021.01)
*A61M 60/13* (2021.01)
*A61M 60/139* (2021.01)
*A61M 60/237* (2021.01)
*A61M 60/268* (2021.01)
*A61M 60/295* (2021.01)
*A61M 60/38* (2021.01)
*A61M 60/857* (2021.01)

(52) U.S. Cl.
CPC .......... *A61M 1/77* (2021.05); *A61M 25/0668* (2013.01); *A61M 39/0247* (2013.01); *A61M 39/0606* (2013.01); *A61M 60/113* (2021.01); *A61M 60/13* (2021.01); *A61M 60/139* (2021.01); *A61M 60/237* (2021.01); *A61M 60/268* (2021.01); *A61M 60/295* (2021.01); *A61M 60/38* (2021.01); *A61M 60/857* (2021.01); *A61M 2039/0273* (2013.01); *A61M 2039/0626* (2013.01)

(56) References Cited

U.S. PATENT DOCUMENTS

| | | | |
|---|---|---|---|
| 9,306,878 B2* | 4/2016 | Patil | G06N 20/00 |
| 9,937,319 B1* | 4/2018 | Leeflang | A61M 25/0668 |
| 10,576,258 B2 | 3/2020 | Fantuzzi et al. | |
| 2002/0177869 A1* | 11/2002 | Eidenschink | A61M 25/09041 |
| | | | 606/194 |
| 2003/0088213 A1* | 5/2003 | Schweikert | A61M 25/0097 |
| | | | 604/533 |
| 2004/0059298 A1 | 3/2004 | Sanderson | |
| 2005/0197624 A1* | 9/2005 | Goodson | A61M 25/0662 |
| | | | 604/96.01 |
| 2006/0047266 A1* | 3/2006 | Elkins | A61M 25/0662 |
| | | | 604/528 |
| 2006/0079859 A1 | 4/2006 | Elkins et al. | |
| 2008/0188831 A1 | 8/2008 | Bonnette et al. | |
| 2009/0259200 A1* | 10/2009 | Lampropoulos | A61M 39/0613 |
| | | | 604/249 |
| 2010/0100044 A1* | 4/2010 | Ye | A61M 25/0668 |
| | | | 604/167.03 |
| 2011/0004223 A1* | 1/2011 | Leeflang | A61M 39/0693 |
| | | | 606/108 |
| 2011/0077621 A1* | 3/2011 | Graham | A61M 39/1011 |
| | | | 604/528 |
| 2014/0025037 A1* | 1/2014 | Elkins | A61M 25/0071 |
| | | | 604/508 |
| 2019/0216995 A1 | 7/2019 | Kapur et al. | |

FOREIGN PATENT DOCUMENTS

| | | | |
|---|---|---|---|
| JP | 2000279527 A | 10/2000 | |
| JP | 2005506133 A | 3/2005 | |
| JP | 2006513809 A | 4/2006 | |
| JP | 2009509644 A | 3/2009 | |
| JP | 2010533568 A | 10/2010 | |
| JP | 2011510686 A | 4/2011 | |
| WO | 9851364 A1 | 11/1998 | |
| WO | WO-0197879 A1 * | 12/2001 | ............ A61M 1/122 |
| WO | 03033049 A2 | 4/2003 | |
| WO | 2004034767 A2 | 4/2004 | |
| WO | 2008079828 A2 | 7/2008 | |
| WO | 2009002828 A2 | 12/2008 | |
| WO | 2009012473 A2 | 1/2009 | |

OTHER PUBLICATIONS

U.S. Appl. No. 62/797,527, filed Jan. 28, 2019.
U.S. Appl. No. 62/777,598, filed Dec. 10, 2018.
U.S. Appl. No. 16/244,998, filed Jan. 10, 2019.
International Search Report and Written Opinion for Application No. PCT/US2020/022021 dated May 29, 2020.
Office Action from corresponding Japanese Patent Application No. 2021-554716 dated Feb. 22, 2024 (15 pp.).
Search Report and Written Opinion from corresponding Singapore Patent Application No. 11202109140V dated Oct. 9, 2023 (11 pp.).
Office Action from corresponding Japanese Patent Application No. 2021-554716 dated Oct. 10, 2024 (10 pp.).
Office Action from corresponding Indian Patent Application No. 202117044530 dated Jan. 15, 2025 (7 pp.).
Office Action from corresponding Australian Patent Application No. 2020234566 dated Oct. 21, 2024 (3 pp.).

* cited by examiner

DUAL HUB INTRODUCER SHEATH

CROSS-REFERENCE TO RELATED APPLICATIONS

The present application claims priority to U.S. Provisional Application No. 62/817,901, filed Mar. 13, 2019, the contents of which are fully incorporated herein by reference.

BACKGROUND

Currently, percutaneous mechanical support devices are leveraged for a variety of clinical indications. Such support devices may comprise, but are not limited to, an Impella® pump, an Extracorporeal Membrane Oxygenation (ECMO) pump, and a balloon pump. The Impella® pump may further comprise an Impella2.5® pump, an Impella5.0® pump, an Impella CP® pump and an Impella LD® pump, all of which are by Abiomed, Inc. of Danvers, MA Most often they are inserted into a patient percutaneously through a single access point (e.g., radial access, femoral access, axillary access) while other procedures, such as, for example, percutaneous coronary intervention (PCI) are performed through a second access point, such as a contralateral femoral or radial access point. The use of multiple devices on a patient at the same time therefore often requires multiple access sites which presents several challenges.

BRIEF SUMMARY

The present technology relates to systems and methods for percutaneously delivering a first medical device and a second medical device to a patient.

In one aspect, the disclosure describes an introducer system comprising: an introducer sheath having a longitudinal axis and a lumen formed therein; and a hub coupled to a proximal end of the introducer sheath. The hub comprises: a first arm having a first lumen and a first hemostasis valve, the first lumen and the first hemostasis valve configured for the passage of a first medical device; a second arm coupled to the first arm and having a second lumen and a second hemostasis valve, the second lumen and the second hemostasis valve configured for the passage of a second medical device; and a connection port coupled to the introducer sheath and to the first arm and the second arm, such that the first lumen and the second lumen are in communication with the lumen of the introducer sheath to allow the passage of at least one of the first medical device and the second medical device through the introducer sheath for delivery to a patient. In some aspects, the first arm is arranged parallel to the longitudinal axis of the introducer sheath. In some aspects, the second arm is configured to branch off the first arm at an angle of no more than 90°. In some aspects, the first arm and the second arm are arranged in a Y-shaped configuration with respect to the introducer sheath. In some aspects, the second arm is located proximal to the connection port. In some aspects, the first arm and the second arm each has a proximal end and a distal end, and the distal end of the first arm is positioned distal of the proximal end of the second arm. In some aspects, the second lumen merges with the first lumen within the hub. In some aspects, the introducer sheath comprises a single lumen for the passage of the first and second medical devices. In some aspects, the first lumen and the second lumen are maintained as separate lumens within the hub. In some aspects, the introducer sheath comprises a dual lumen sheath such that the first lumen is in communication with one of the lumens of the dual lumen sheath, and the second lumen is in communication with the other lumen of the dual lumen sheath. In some aspects, the introducer sheath is an expandable sheath. In some aspects, the introducer sheath is a peel-away sheath. In addition, the hub may further comprise tabs to enable separation of the hub and the peel-away sheath. In some aspects, the first and second hemostasis valves are configured to seal the respective first and second lumens. In some aspects, the first and second hemostasis valves are each configured to be penetrable by the first or second medical device. In some aspects, the hub further comprises at least one suture ring. In some aspects, the first arm and the second arm each comprise at least one side-port. In addition, the side-port may comprise an irrigation port configured to be supplied with an irrigation fluid. In some aspects, at least one of the first arm and the second arm comprises a locking mechanism configured to prevent axial movement of one or both of the first medical device and the second medical device within the introducer sheath after delivery to the patient. In some aspects, the locking mechanism comprises at least one of: a Tuohy-Borst adaptor, an inflatable balloon, and a locking lever arm. In some aspects, the locking mechanism is biased in a state that is configured to prevent axial movement of one or both of the first medical device and the second medical device within the introducer sheath. In some aspects, the introducer sheath comprises at least one of: a polyether block amide; a polyethylene material; a polytetrafluoroethylene (PTFE) material; a high-density polyethylene (HDPE) material; a medium-density polyethylene (MDPE) material; or a low-density polyethylene (LDPE) material. In some aspects, the hub comprises at least one of: ethylene-vinyl acetate (EVA); styrene-butadiene copolymer (SBC); styrene ethylene butylene styrene (SEBS); a high-density polyethylene (HDPE) material; a medium-density polyethylene (MDPE) material; a low-density polyethylene (LDPE) material; polyether ether ketone (PEEK); a polyether block amide; an elastomer; synthetic rubber; or a polyethylene, polyurethane, or polycarbonate material with an elastic modulus of about 40 ksi. In some aspects, the first medical device is a mechanical circulatory support device, and the second medical device is a coronary reperfusion therapy device for providing the patient with percutaneous coronary intervention (PCI). In some aspects, the coronary reperfusion therapy device is a stent. In some aspects, the stent is configured for insertion through the second arm and introducer sheath by a catheter. In some aspects, the mechanical circulatory support device comprises at least one of: a blood pump; a transvalvular axial-flow (TV)-pump; an intra-aortic balloon pump; or an extracorporeal membrane oxygenation (ECMO) pump. In some aspects, the mechanical circulatory support device is a rotary blood pump having a cannula and a rotor and rotor housing. In some aspects, the first arm and the introducer sheath are configured to allow passage of the cannula of the rotary blood pump. In some aspects, the first arm and the introducer sheath are configured to allow passage of the rotor and rotor housing of the rotary blood pump. In some aspects, the hub comprises up to five second arms, each second arm configured with a hemostasis valve and a lumen in communication with the introducer sheath for the passage of the second medical device from a respective second arm into the introducer sheath. In some aspects, the second arms are arranged in a radially symmetric manner about the first arm. In some aspects, the hub comprises two second arms. In some aspects, the introducer system may further comprise at least one third arm coupled to the first arm, each third arm having a third lumen and a third hemostasis valve, the third lumen and third hemostasis valve configured for the passage of a third medical device.

In another aspect, the disclosure describes a method comprising: inserting a first medical device into a first arm of an introducer hub, the first arm having a first lumen for the passage of the first medical device therethrough; inserting a second medical device into a second arm attached to the first arm, the second arm having a second lumen for the passage of the second medical device therethrough; providing the first medical device and the second medical device to an introducer sheath via a connector port of an introducer hub, the connector port coupled to a proximal end of the introducer sheath; and delivering the first medical device and the second medical device to a patient from a distal end of the introducer sheath. In some aspects, the method further comprises inserting the first and second medical devices into a lumen formed within the introducer sheath for delivery to the patient. In some aspects, the method further comprises inserting the first medical device into a first lumen formed within the introducer sheath for delivery to the patient, and inserting the second medical device into a second lumen formed within the introducer sheath for delivery to the patient, the first lumen isolated from the second lumen. In some aspects, the method further comprises attaching the introducer hub to the patient via a suture ring. In some aspects, the method further comprises providing one or both of the first lumen and the second lumen with an irrigation fluid via a side-port positioned on each of the first and second arms. In some aspects, the method further comprises activating a locking mechanism to prevent axial movement of one or both of the first medical device and the second medical device within the introducer sheath. In some aspects, the locking mechanism comprises at least one of: a Tuohy-Borst adaptor, an inflatable balloon, and a locking lever arm. In some aspects, the locking mechanism is biased in a state that prevents axial movement of one or both of the first medical device and the second medical device within the introducer sheath. In some aspects, the method further comprises inserting a third medical device into a third arm attached to the first arm, the third arm having a third lumen for the passage of the third medical device therethrough for delivery to the patient. In some aspects, the method further comprises supporting the patient's heart that has sustained myocardial infarction. In some aspects, the method further comprises: inserting the first medical device through the first arm and through the introducer sheath into the patient's left ventricle; operating the first medical device for a support period of greater than 30 minutes at a rate of at least 2.5 L/min of blood flow; inserting the second medical device through the second arm and through the introducer sheath into a coronary vessel of the patient; and operating the second medical device after the support period has elapsed. In some aspects, the first device comprises a mechanical circulatory support device. In some aspects, the mechanical circulatory support device comprises at least one of: a blood pump, a transvalvular axial-flow (TV)-pump, an intra-aortic balloon pump, or an extracorporeal membrane oxygenation (ECMO) pump. In some aspects, the second device comprises a coronary reperfusion therapy device for providing the patient with percutaneous coronary intervention (PCI). In some aspects, the mechanical circulatory support device is operated to pump blood from the patient's left ventricle into the patient's aorta during the support period. In some aspects, the second medical device is inserted through the second arm after the first medical device is positioned across the patient's aortic valve and is unloading the patient's left ventricle. In some aspects, the second medical device is inserted through the introducer sheath at least 15 minutes after the first medical device begins unloading the patient's left ventricle. In some aspects, the first medical device is positioned with a distal tip located within the patient's left ventricle and pumps blood from the patient's left ventricle into the patient's aorta. In some aspects, the introducer hub comprises up to five second arms, each second arm configured with a hemostasis valve and a lumen in communication with the introducer sheath for the passage of the second medical device from a respective second arm into the introducer sheath. In some aspects, the second arms are arranged in a radially symmetric manner about the first arm. In some aspects, the introducer hub comprises two second arms. In some aspects, the introducer hub further comprises at least one third arm coupled to the first arm, each third arm having a third lumen and a third hemostasis valve, the third lumen and third hemostasis valve configured for the passage of a third medical device.

In another aspect, the disclosure describes an introducer hub comprising: a first arm having a first lumen and a first hemostasis valve, the first lumen and first hemostasis valve configured for the passage of a first medical device; a second arm coupled to the first arm and having a second lumen and a second hemostasis valve, the second lumen and second hemostasis valve configured for the passage of a second medical device; and a connection port coupled to an introducer sheath and to the first arm and the second arm, such that the first lumen and the second lumen are in communication with the lumen of the introducer sheath to allow the passage of at least one of the first medical device and the second medical device through the introducer sheath for delivery to a patient. In some aspects, the first arm is arranged parallel to a longitudinal axis of the introducer sheath. In some aspects, the second arm is configured to branch off the first arm at an angle of no more than 90°. In some aspects, the first arm and the second arm are arranged in a Y-shaped configuration with respect to the introducer sheath. In some aspects, the second arm is located proximal to the connection port. In some aspects, the first arm and the second arm each has a proximal end and a distal end, and the distal end of the first arm is positioned distal of the proximal end of the second arm. In some aspects, the second lumen merges with the first lumen. In some aspects, the introducer sheath comprises a single lumen for the passage of the first and second medical devices. In some aspects, the first lumen and the second lumen are maintained as separate lumens. In some aspects, the introducer sheath comprises a dual lumen sheath such that the first lumen is in communication with one of the lumens of the dual lumen sheath, and the second lumen is in communication with the other lumen of the dual lumen sheath. In some aspects, the introducer sheath is an expandable sheath. In some aspects, the introducer sheath is a peel-away sheath. In some aspects, the introducer hub further comprises tabs to enable separation of the introducer hub and the peel-away sheath. In some aspects, the first and second hemostasis valves are configured to seal the respective first and second lumens. In some aspects, the first and second hemostasis valves are each configured to be penetrable by the first or second medical device. In some aspects, the introducer hub further comprises at least one suture ring. In some aspects, the first arm and the second arm each comprise at least one side-port. In some aspects, the side-port comprises an irrigation port configured to be supplied with an irrigation fluid. In some aspects, at least one of the first arm and the second arm comprises a locking mechanism configured to prevent axial movement of one or both of the first medical device and the second medical device within the introducer sheath after delivery to the patient. In some aspects, the locking mechanism comprises at least one of: a Tuohy-Borst adaptor, an inflatable balloon, and a locking lever arm. In some aspects, the locking mechanism is biased in a state that is configured to prevent axial movement of one or both of the first medical device and the second medical device within the introducer sheath. In some aspects, the introducer hub comprises up to five second arms, each second arm configured with a hemostasis valve and a lumen in communication with the introducer sheath for the passage of the second medical device from a respective second arm into the introducer sheath. In some aspects, the second arms are arranged in a radially symmetric manner about the first arm. In some aspects, the introducer hub comprises two second arms. In some aspects, the introducer hub further comprises at least one third arm coupled to the first arm, each third arm having a third lumen and a third hemostasis valve, the third lumen and the third hemostasis valve configured for the passage of a third medical device. In some aspects, the introducer hub comprises at least one of: ethylene-vinyl acetate (EVA); styrene-butadiene copolymer (SBC); styrene ethylene butylene styrene (SEBS); a high-density polyethylene (HDPE) material; a medium-density polyethylene (HDPE) material; a low-density polyethylene (LDPE) material; polyether ether ketone (PEEK); a polyether block amide; an elastomer; synthetic rubber; or a polyethylene, polyurethane, or polycarbonate material with an elastic modulus of about 40 ksi.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
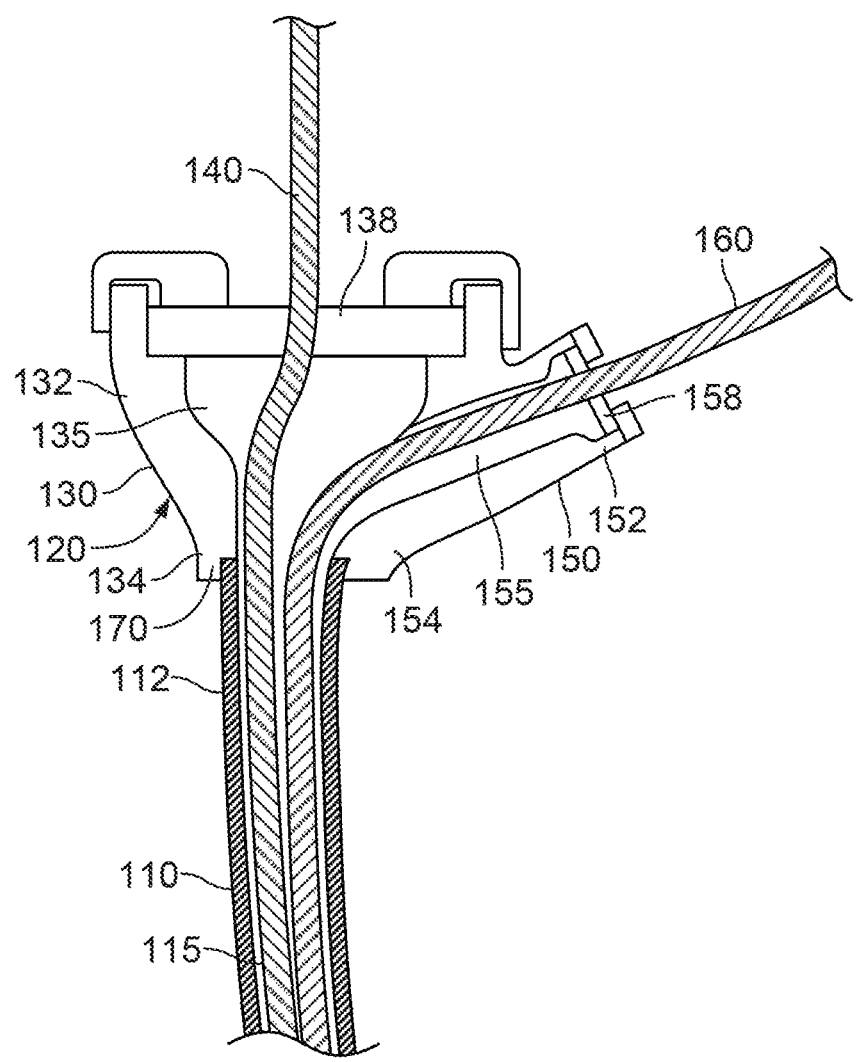
FIG. 1 shows an illustrative cross section of a dual hub introducer sheath system used for delivering a first medical device and second medical device into an arteriotomy of a patient, according to aspects of the disclosure.

To provide an overall understanding of the systems, devices and methods described herein, certain illustrative examples will be described. Although the examples and features described herein are specifically described for use in connection with dual hub introducer sheath for use in intravascular procedures involving catheter based ventricular assist devices, it will be understood that all the components and other features outlined below may be combined with one another in any suitable manner and may be adapted and applied to other types of procedures requiring a dual hub introducer sheath.

As mentioned above, while it is possible to use multiple devices on a patient at the same time using multiple access sites, this can be challenging for a variety of reasons. Firstly, the patient may not have two anatomically available access sites for the PCI procedural devices, in which, for example, two 6-7 Fr sheaths may be used to facilitate procedures such as ballooning and stenting. In addition, peripheral artery disease, vessel lumen size (too small), scar tissue from previous procedures, and other diseases may complicate gaining access to a percutaneous site for larger devices, e.g., mechanical support devices. Using multiple access sites may also increase the likelihood of encountering vascular access complications, which can correlate to increased mortality, added hospital costs, etc. Further, multiple access sites requires more procedural time since access needs to be gained more than once, and can lead to increased procedural costs due to requiring multiple vascular closure devices, additional introducers, etc. There is thus a significant need for reducing the complexity of procedures requiring the operation of multiple devices on a patient.

The systems, devices and methods described herein relate to a dual hub introducer sheath which enables a single access site for multiple devices. For purposes of illustration herein, but not by way of limitation, the devices are described as a mechanical assist device (such as, for example, an Impella device) and a device for the PCI procedure. However, one skilled in the art will understand that the present disclosure is not limited to any particular kind of percutaneously inserted device. In fact, the disclosure contemplates that, in some aspects of the technology, the multiple devices can be two of the same device. Until recently, such single access for multiple devices has not been apparently possible because physicians were unaware of the ability to fit both the PCI device and the Impella device through a single sheath without increasing the overall diameter of the sheath.

Successful insertion of PCI devices through the same access sheath as the Impella device to perform both PCI and Impella support in a single access site has recently been reported (M. L. Esposito et al., "Left Ventricular Unloading Before Reperfusion Promotes Functional Recovery After Acute Myocardial Infarction," Journal of the American College of Cardiology, Elsevier, vol. 72, no. 5, May 2018). However, using the current solutions leads to issues with hemostasis from the introducer valve and pump migration into and out of the ventricle as PCI devices are exchanged and manipulated. These adverse effects arise because conventional introducer valves are simply not designed to be accessed by dual devices.

The devices and methods described herein relate to a dual hub introducer sheath having a longitudinal axis and a lumen formed therein. The sheath also comprises a hub coupled to a proximal end of the introducer sheath. The hub comprises a first arm having a first lumen and a first hemostasis valve, the first lumen and hemostasis valve configured for the passage of a first medical device. The hub also comprises a second arm coupled to the first arm and having a second lumen and a second hemostasis valve, the second lumen and hemostasis valve configured for the passage of a second medical device. Further, the hub comprises a connection port coupled to the introducer sheath and to the first arm and the second arm, such that the first lumen and the second lumen are in communication with the lumen of the introducer sheath to allow the passage of at least one of the first medical device and second medical device through the introducer sheath for delivery to the patient.

The dual hub introducer sheath of the present disclosure allows for both the PCI and Impella device to be inserted through it while maintaining appropriate and acceptable hemostasis. By leveraging a bifurcated hub, two separate valves can be implemented which are specifically designed to meet insertion force and leakage requirements for either the Impella device or the PCI device, noting that these requirements and designs are quite different. Additionally, the dual hub introducer sheath of the present disclosure has a locking mechanism isolated to an arm of the hub intended for the Impella device which the physician can activate to hold the Impella in place preventing it from advancing or retracting as the PCI procedure is performed.

FIG. 1 shows a dual hub introducer sheath delivery system 100 for percutaneously delivering a first medical device and a second medical device to a patient. System 100 comprises introducer sheath 110 that extends between a proximal end 112 and a distal end (not shown) along a longitudinal axis (not shown). Sheath 110 further comprises a lumen 115 that extends between the proximal end 112 and distal end for the passage of the first medical device and the second medical device. While FIG. 1 depicts a sheath 110 having a single lumen 115, in some aspects of the technology, sheath 110 may comprise two distinct lumens throughout the length of the sheath, for example. In other aspects of the technology, sheath 110 may comprise any number of distinct lumens. System 100 further comprises a hub 120 coupled to the proximal end 112 of the sheath 110.

Hub 120 comprises a first arm 130 having a proximal end 132 and a distal end 134, the first arm 130 defining a first lumen 135. A first valve 138 is provided at the proximal end 132 of the first arm 130 to seal the first lumen 135 from the ambient. The first valve 138 is penetrable by the first medical device 140. Hub 120 further comprises a second arm 150 attached to the first arm 130. As with the first arm 130, second arm 150 defines a second lumen 155 and comprises a proximal end 152 and a distal end 154. A second valve 158 is provided at the proximal end 152 of the second arm 150 to seal the second lumen 155 from the ambient. The second valve 158 is penetrable by the second medical device 160. In some aspects of the technology, the first valve 138 and the second valve 158 may comprise hemostasis valves (also referred to as "hemostatic" valves), such as, for example the valve described in U.S. Pat. No. 10,576,258 entitled "Hemostatic Valve for Medical Device Introducer," the entire contents of which are hereby incorporated by reference herein. While FIG. 1 shows a hub 120 comprising one second arm 150, it will be understood that the hub 120 may comprise any number of second arms arranged relative to the first arm 130.

The hub 120 further comprises a connection port 170 which connects to the first lumen 135 and the second lumen 155. The connection port 170 of the hub 120 is coupled to the proximal end 112 of the sheath 110 such that the first medical device 140 and the second medical device 160 may traverse the sheath 110 to be delivered to a patient when the sheath 110 is inserted in the patient. In some aspects of the technology, such coupling may be a friction fit, for example, in which the proximal end 112 of the sheath 110 is dimensioned such that a friction fit between the outer surface of the sheath 110 and the inner surface of the connection port 170 prevents the proximal end 112 of the sheath 110 from detaching from the hub 120. In other aspects of the technology, the coupling may be brought about by an external thread on the outer surface of the proximal end 112 of the sheath 110 which interacts with a complementary thread on the inner surface of the connection port 170, for example. In further aspects of the technology. the sheath 110 may be coupled to the connection port 170 in any manner that enables the first lumen 135 and the second lumen 155 to be fluidically connected to the lumen 115 of the sheath 110 via the connection port 170 of the hub 120. In some aspects of the technology, the hub 120 may be overmolded and press fit or compressed onto the proximal end 112 of the sheath 110.

In some aspects of the technology, the hub 120 may be fabricated such that the first lumen 135 and the second lumen 155 merge within the hub 120 before transitioning into the connection port 170, as shown in FIG. 1. In such cases, the hub 120 may be coupled to a single lumen sheath, such as sheath 110 in FIG. 1, where the lumen 115 of the sheath 110 is in fluid communication with the first lumen 135 and the second lumen 155 via the connection port 170 of the hub 120. Thus, when the first medical device 140 is inserted into the first arm 130 and the second medical device 160 is inserted into the second arm 150 of the hub 120, the medical devices share the same lumen 115 of the sheath 110 when traversing the sheath 110 for delivery to the patient. In other aspects of the technology, the hub 120 may be fabricated such that the first lumen 135 and the second lumen 155 are maintained as separate lumens throughout the hub 120. In such cases, the hub 120 may be coupled to a dual lumen sheath such that the first medical device 140 and the second medical device 160 are separated at all times while traversing the length of the sheath 110 for delivery into an arteriotomy of the patient.

As shown in FIG. 1 the second arm 150 may be arranged such that it branches off the first arm 130 at an angle relative to the first arm 130, and the first arm 130 may be axially aligned with the longitudinal axis of the sheath 110. In some aspects of the technology, this angle is not larger than 90°. In such cases, when the first medical device 140 is inserted into the first arm 130, it is maintained in a substantially straight shape within the hub 120 without having to bend or kink; and when the second device 160 is inserted into the second arm 150, the arrangement of the second arm 150 relative to the first arm 130 causes the second device 160 to bend such that it aligns with the first device 140 before exiting the hub 120 via the connector port 170 and traversing the lumen 115 of the sheath 110.

In some aspects of the technology, the first arm 130 and the second arm 150 may be arranged such that they form a Y-shaped configuration with respect to the longitudinal axis of the introducer sheath 110. In such cases, both the first medical device 140 and the second medical device 160 may bend within the hub 120 such that they are aligned with the longitudinal axis of the sheath 110 as they exit the connector port 170 and traverse the lumen 115 of the sheath 110.

Figure 2:
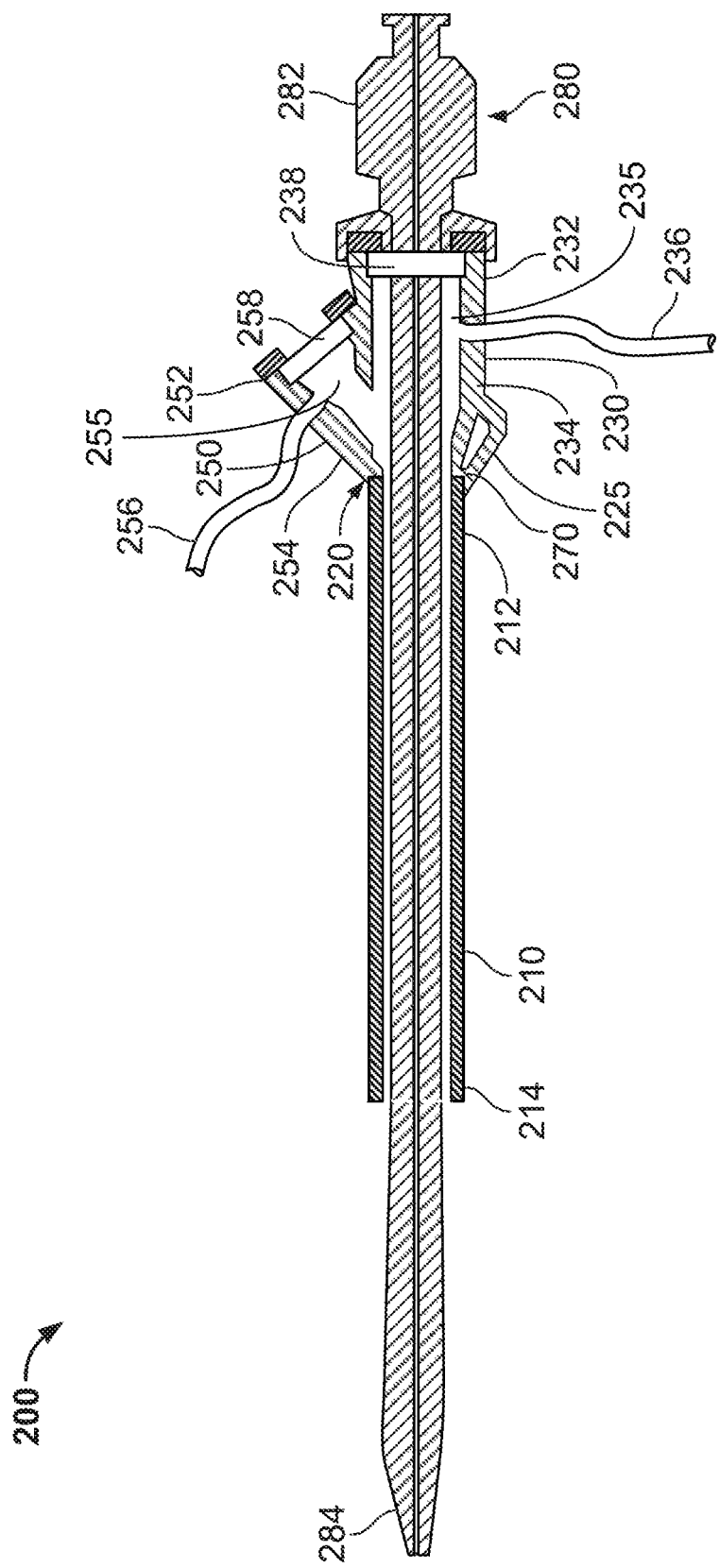
FIG. 2 shows a dual hub introducer sheath system with a dilator for insertion into the arteriotomy of the patient, according to aspects of the disclosure.

FIG. 2 shows the configuration of a dual hub introducer sheath system 200 according to aspects of the technology. Sheath system 200 is similar to sheath system 100 in that it comprises a sheath 210 having a proximal end 212 and a distal end 214 with a lumen extending between the proximal end 212 and the distal end 214 for the passage of at least one medical device, such as the first medical device 140 and the second medical device 160 of FIG. 1, for delivery to an arteriotomy of a patient. The proximal end 212 of the sheath 210 is coupled to a connector port 270 of a hub 220. The hub 220 comprises a first arm 230 having a proximal end 232 and a distal end 234, and a second arm 250 attached to the first arm 230 and having a proximal end 252 and a distal end 254. The first arm 230 forms a first lumen 235 which is sealed from the ambient by a first valve 238. Similarly, the second arm 250 forms a second lumen 255 which is sealed from the ambient by a second valve 258. The first valve 238 and the second valve 258 may comprise a hemostasis valve, and may be penetrable by the first and second medical devices, as has been described in relation to FIG. 1. In some aspects of the technology, the second lumen 255 fluidically connects to the first lumen 235 within the hub 220, as shown in FIG. 2. In other aspects of the technology, the first lumen 235 and the second lumen 255 may be maintained as separate lumens within the hub 220. In some aspects of the technology, the first valve 238 and the second valve 258 may be inserted into position by a snap cap to secure their position within the hub 220.

As shown in FIG. 2 (and the enlargement 300 in FIGS. 3 and 4) the first arm 230 further comprises a first side port 236 that is in fluid connection with the first lumen 235. Similarly, the second arm 250 comprises a second side port 256 that is in fluid communication with the second lumen 255. Side port 236 and side port 256 may each serve as an irrigation port through which irrigation fluid can be injected to free the lumens 235, 255 within the hub 220 of any thrombus that may have formed during treatment of the patient. In other aspects of the technology, the side ports 236, 256 may serve as inflation ports connected to inflatable balloons within the hub 220 that may be inflated with an inflation fluid to expand the balloons so as to anchor or lock the positions of the first medical device 140 and the second medical device 160 relative to the respective arms through which they are inserted. In such cases, the inflated balloon may compress the medical device against its respective arm so as to prevent axial movement of the medical device within the sheath once the device is deployed in the patient. Such locking mechanisms for securing the position of a medical first device to prevent axial motion during insertion or manipulation of a second medical device using internal sheath balloons are known to those skilled in the art. For example, various locking mechanisms for securing the position of a first medical device to prevent axial motion during insertion or manipulation of a second medical device using internal sheath balloons are described in U.S. Provisional Patent Application No. 62/797,527, the entire contents of which are hereby incorporated by reference herein. Other locking mechanisms will be detailed in the foregoing sections. While only one side port is shown on each arm in FIGS. 2 and 3, any number of side ports may be used on each arm within the scope of the present disclosure.

As discussed above, the second arm 250 may be arranged on the first arm 230 and configured to branch off the first arm 230 at an angle of no more than 90° with respect to the longitudinal axis of the sheath 210. Additionally, in some aspects of the technology, the distal end 254 of the second arm 250 may be positioned proximal to the connector port 270, and the proximal end 232 of the first arm 230 may be positioned distal to the connector port 270. In this manner the proximal end 252 of the second arm 250 may be sufficiently spaced apart from the proximal end 232 of the first arm 230 to allow the first and second medical devices to interact with the respective arms 230, 250 without having to abut each other.

Figure 3:
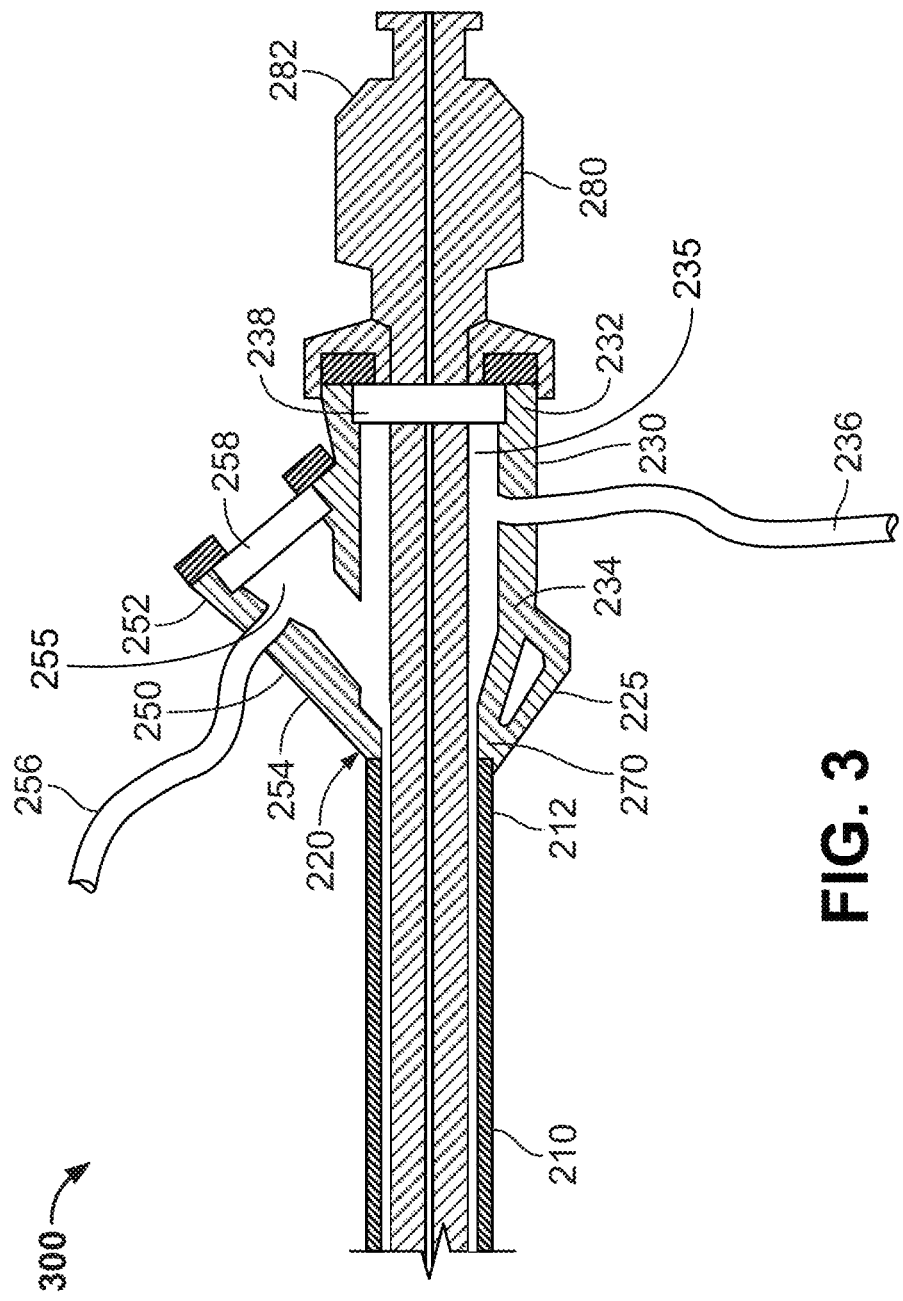
FIG. 3 shows a detailed view of the dual hub introducer sheath system of FIG. 2.

As seen in FIGS. 2 and 3, the hub 220 may optionally include a suture ring 225 to aid with the attachment of the hub 220 to the patient after the first and second medical devices have been inserted in the patient. In certain aspects of the technology, the suture ring 225 may be positioned proximal to the connector port 270 as the profile of the hub 220 in this location may be smaller than at locations proximal to either the first arm 230 or the second arm 250. In other aspects of the technology, the suture ring 225 may be located at any location along the body of hub 220. While only one suture ring is shown in FIGS. 2 and 3, it will be understood that any number of suture rings may be present to aid in securing the hub 220 to the patient.

In order to insert the introducer sheath 210 into the patient, a dilator 280 may be used in connection with the dual hub 220. FIGS. 2 and 3 also show a dilator 280 that has been inserted into the first arm 230 of the hub 220. The dilator 280 comprises a proximal end 282 and a distal end 284. The length of the dilator is such that the distal end 284 extends beyond the distal end 214 of the sheath 210 when the dilator 280 is fully inserted into the 210. As previously mentioned, while the first arm 230 and the second arm 250 may assume any configuration relative to the longitudinal axis of the sheath 210 (e.g., a Y-shaped configuration), where insertion of the introducer sheath 210 into the patient requires a dilator 280, the first arm 230 may be axially aligned with the longitudinal axis of the sheath 210. With this arrangement of the first arm 230, the dilator does not need to bend when being inserted in to the hub 220, which may allow for a greater force to be applied when inserting the sheath 210 into the patient. Once inserted, proximal end 282 of the dilator 280 may connect to the proximal end 232 of the first arm 230. This may be accomplished by any suitable type of connection, such as through a press fit or a twist connection.

Figure 4:
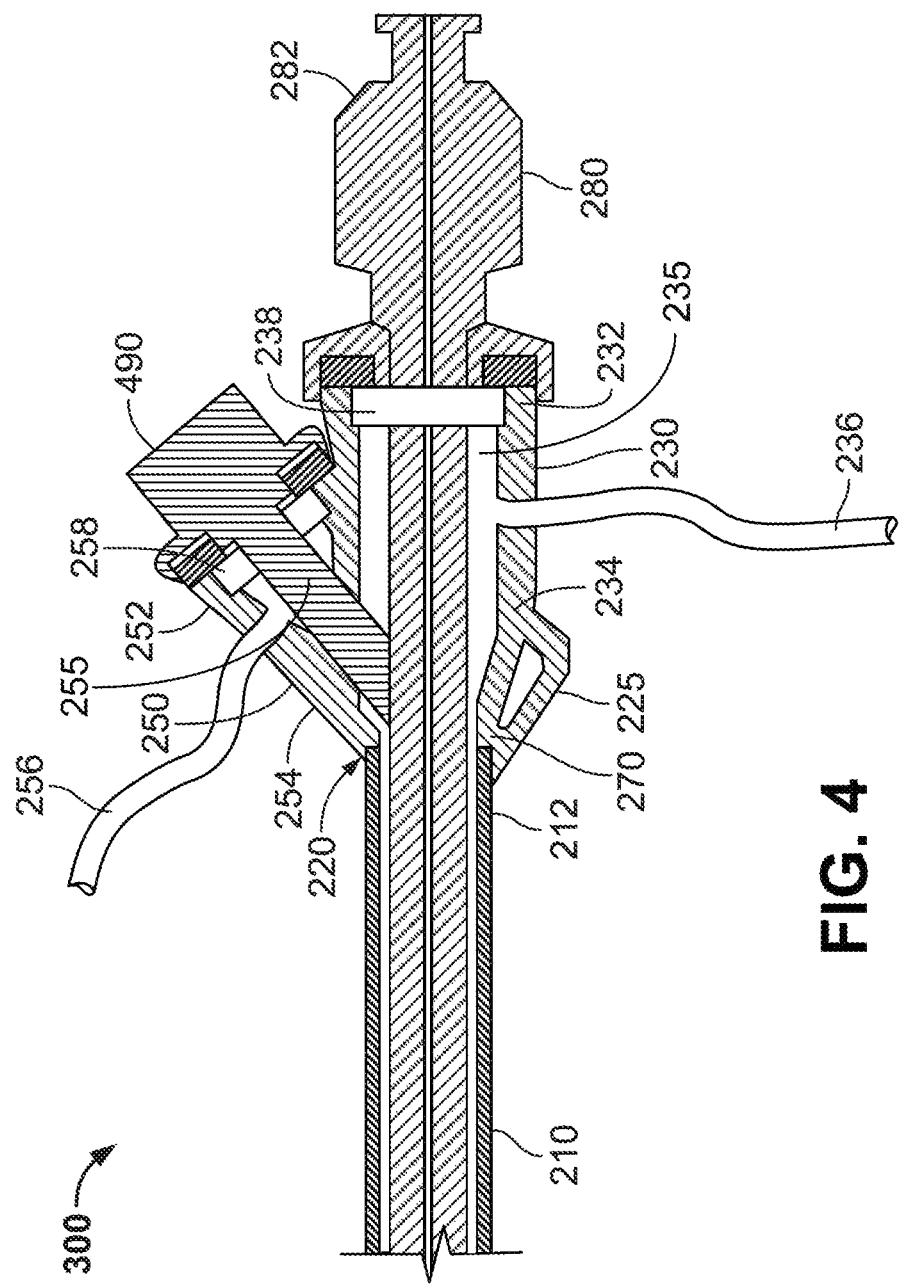
FIG. 4 shows a detailed view of the dual hub introducer sheath system of FIG. 2 with an occulder sealing a lumen in a side arm.

In some aspects of the technology, an occluder 490 may be inserted into the lumen 255 of the second arm 250, as shown in FIG. 4. Such an occluder 490 may be inserted to prevent any backflow of fluid when the sheath 210 is inserted into the patient. This may be helpful in cases where sheath 210 needs to be repositioned after the medical devices have been removed from the first arm 230 and the second arm 250. In such situations, due to their prior use, the respective seals 238, 258 may not be able to seal the lumens 235, 255 from the ambient completely due to wear and tear. As with the dilator 280, the occluder 490 may connect to the proximal end 252 of the second arm 250 by any suitable type of connection, such as through a press fit or a twist connection.

Figure 5A:
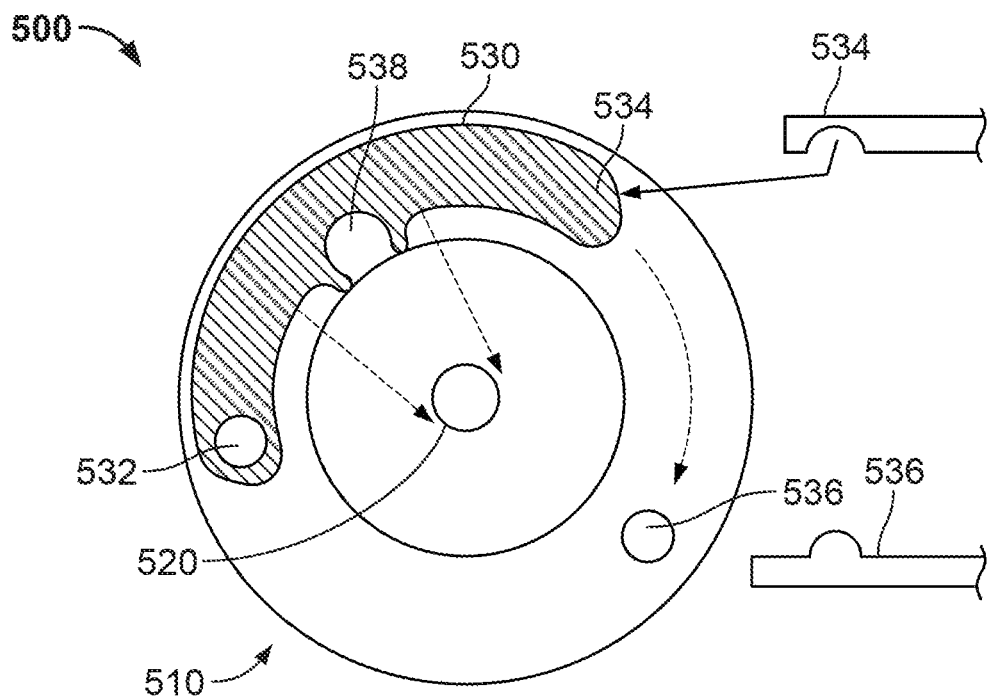
FIG. 5A shows an illustrative locking mechanism, in an open state, used in a dual hub introducer sheath system according to aspects of the disclosure.
Figure 5B:
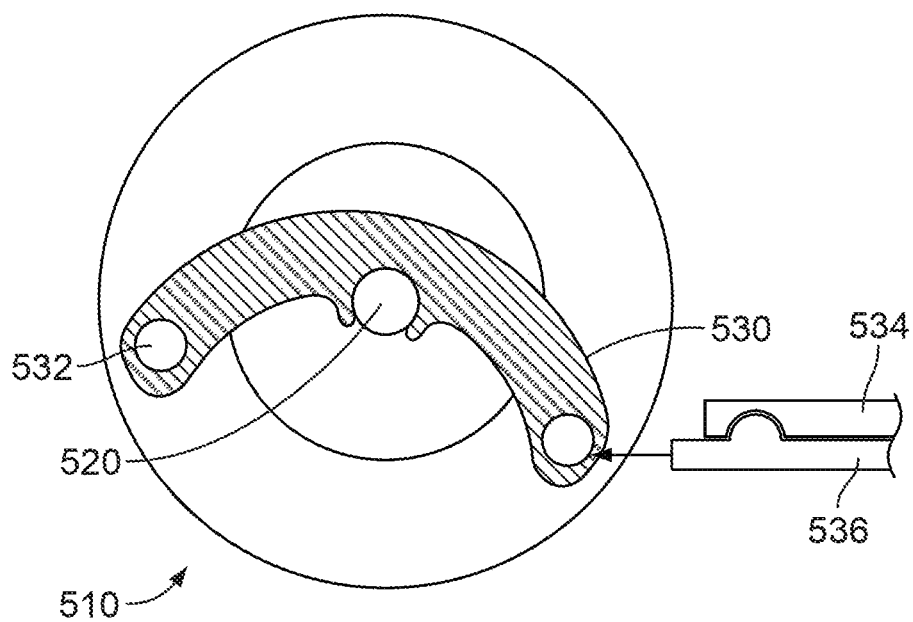
FIG. 5B shows the locking mechanism of FIG. 5A in a locked state.

As mentioned in the foregoing, the first medical device 140 and the second medical device 160 may be axially constrained by a locking mechanism. In some aspects of the technology, a locking mechanism may be configured so that some action must be taken in order to lock and/or unlock it. In some aspects of the technology, a locking mechanism may have a bias. For example, in some aspects of the technology, a locking mechanism may be biased in an unlocked state such that it does not restrict movement of the medical device unless an action is taken to lock the locking mechanism. Conversely, in some aspects of the technology, a locking mechanism may be biased in a locked state such that it restricts movement of the medical device unless an action is taken to unlock the locking mechanism. In some aspects of the technology, the locking mechanism may comprise an internal balloon located within the first lumen 235 or the second lumen 255, the internal balloon being inflated by a side arm 236, 256, as previously described. In some aspects of the technology, the locking mechanism may also comprise a locking lever arm as shown in FIGS. 5A and 5B. FIG. 5A shows the cross section of a hub 510 similar to hubs 220 and 120 as described in the foregoing. Hub 510 is shown with a first medical device 520 traversing therethrough, although it will be appreciated that the hub 510 may be allow the passage of a plurality of medical devices. Hub 510 also comprises a lever arm 530 which may be a separate component which is positioned within the hub body. The lever arm 530 may be configured to have a semicircular shape as shown in FIGS. 5A and 5B, however any shape of arm may be used that is suitable to secure the medical device 520 and prevent axial motion thereof.

The lever arm 530 may be pivotally connected to the hub 510 at a point 532 as shown in FIG. 5A. In the unlocked position, the lever arm 530 resides within the hub body. The lever arm may comprise an actuating mechanism such as a handle or tab (not shown) that is accessible from the exterior of the hub 510. The lever arm 530 comprises a notch or catch 538 that is configured to fit around the external periphery of the medical device 520 when the lever arm 530 is in the locked position. In this position, as shown in FIG. 5B, the notch 538 pinches the medical device 520 to increase axial friction. In some aspects of the technology, the notch 538 may bend the medical device 520 when the lever arm 530 is in the locked position. In some aspects of the technology, the lever arm 530 may be located at the respective hemostasis valves 238, 258. Additionally, to secure the lever arm in the locked position, the end 534 of the lever arm 530 may be configured with a recess on its distal surface that engages with a protrusion 536 located within the hub body. The side profiles of end 534 and protrusion 536 are shown in FIG. 5A. Similarly, FIG. 5B shows end 534 in engagement with protrusion 536. In some aspects of the technology, the lever arm 530 may be overmolded with a high friction material such as a low-durometer polyurethane or a silicone.

In addition to, or as an alternative to, the locking mechanisms described in the foregoing, the dual hub of the present disclosure may also comprise a Tuohy Borst mechanism built into the first or second arms of the hub body. Such a mechanism comprises a silicone slug that reduces in inner diameter onto the first and/or second medical device traversing the respective arm, thereby securing the position of the medical device.

As noted above, in some aspects of the technology, the sheath 210 may comprise a dual lumen sheath. In such a case, when the dual lumen sheath is coupled to the hub 220, the first lumen 235 of the hub 220 may be in fluid communication with one of the lumens of the dual lumen sheath, and the second lumen 255 of the hub 220 may be communication with the other lumen of the dual lumen sheath.

In some aspects of the technology, the sheath 210 may comprise an expandable sheath. Expandable sheaths are well known to those skilled in the art and are not described in detail herein. For example, various expandable sheaths are described in U.S. Provisional Patent Application No. 62/797,527, which has been incorporated by reference herein.

In some aspects of the technology, the sheath 210 may comprise a peel-away sheath. Peel-away sheaths are also well known to those skilled in the art and are not described in detail herein. For example, various peel-away sheaths are described in U.S. Provisional Patent Application No. 62/777,598, the entire contents of which are hereby incorporated by reference herein. Peel-away sheaths may comprise one or more lines of weakness that are formed within the sheath body and extend longitudinally along the sheath to allow the sheath to be pulled apart as needed during treatment of the patient.

In some aspects of the technology, the hub 220 may comprise tabs that enable the hub 220 itself to be separated when it is no longer needed, e.g., when one or more of the medical devices are positioned within the patient.

In some aspects of the technology, the sheath 210 may be extruded and/or laminated. In some aspects of the technology, the introducer sheath 110, 210 may comprise at least one of: a polyether block amide (such as PEBAX® or PebaSlix®); a polyethylene material; a polytetrafluoroethylene (PTFE) material; a high-density polyethylene (HDPE) material; a medium-density polyethylene (MDPE) material; or a low-density polyethylene (LDPE) material.

Further, as described above, in some aspects of the technology, the hub 120, 220 may be formed by overmolding. In some aspects of the technology, the hub 120, 220 may comprise at least one of: ethylene-vinyl acetate (EVA); styrene-butadiene copolymer (SBC); styrene ethylene butylene styrene (SEBS); a high-density polyethylene (HDPE) material; a medium-density polyethylene (MDPE) material; a low-density polyethylene (LDPE) material; polyether ether ketone (PEEK); a polyether block amide (such as PEBAX® or PebaSlix®); an elastomer; synthetic rubber; a polyethylene, polyurethane, or polycarbonate material with an elastic modulus of about 40 ksi; a crack-resistant material; or a material with a low coefficient of friction.

As mentioned in the foregoing description, the dual hub introducer sheath of the present disclosure is designed to facilitate the traversal of catheter-based medical devices (such as the first medical device and the second medical device) within the lumen of an introducer sheath. In some aspects of the technology, the first medical device is a mechanical circulatory support device, and the second medical device is a coronary reperfusion therapy device for providing the patient with percutaneous coronary intervention (PCI). These PCI procedures may involve the use of a coronary stent delivered into the distal left anterior descending artery (LAD). Examples of such coronary stents include, but are not limited to, the Promus PREMIER™ and the REBEL™ bare-metal Platinum Chromium Coronary Stents, and the SYNERGY™ Bioabsorbable Polymer Stent, all by Boston Scientific, Marlborough, MA In some aspects of the technology, the mechanical circulatory support device may comprise a rotary blood pump having a cannula, a rotor, and rotor housing. Examples of such blood pumps include, but are not limited to, an Impella® pump, an Extracorporeal Membrane Oxygenation (ECMO) pump, and a balloon pump. The Impella® pump may further comprise an Impella 2.5® pump, an Impella 5.0® pump, an Impella CP® pump, or an Impella LD® pump, all of which are by Abiomed, Inc. of Danvers, MA.

In some aspects of the technology, the first medical device and the second medical device may be used with the dual hub introducer sheath as described in the foregoing in procedures where PCI and percutaneous ventricular assist devices are used in unison, such as, for example, the method of left ventricular unloading in treating myocardial infarction as described in U.S. patent application Ser. No. 16/244,998, the entire contents of which are hereby incorporated by reference herein.

Figure 6:
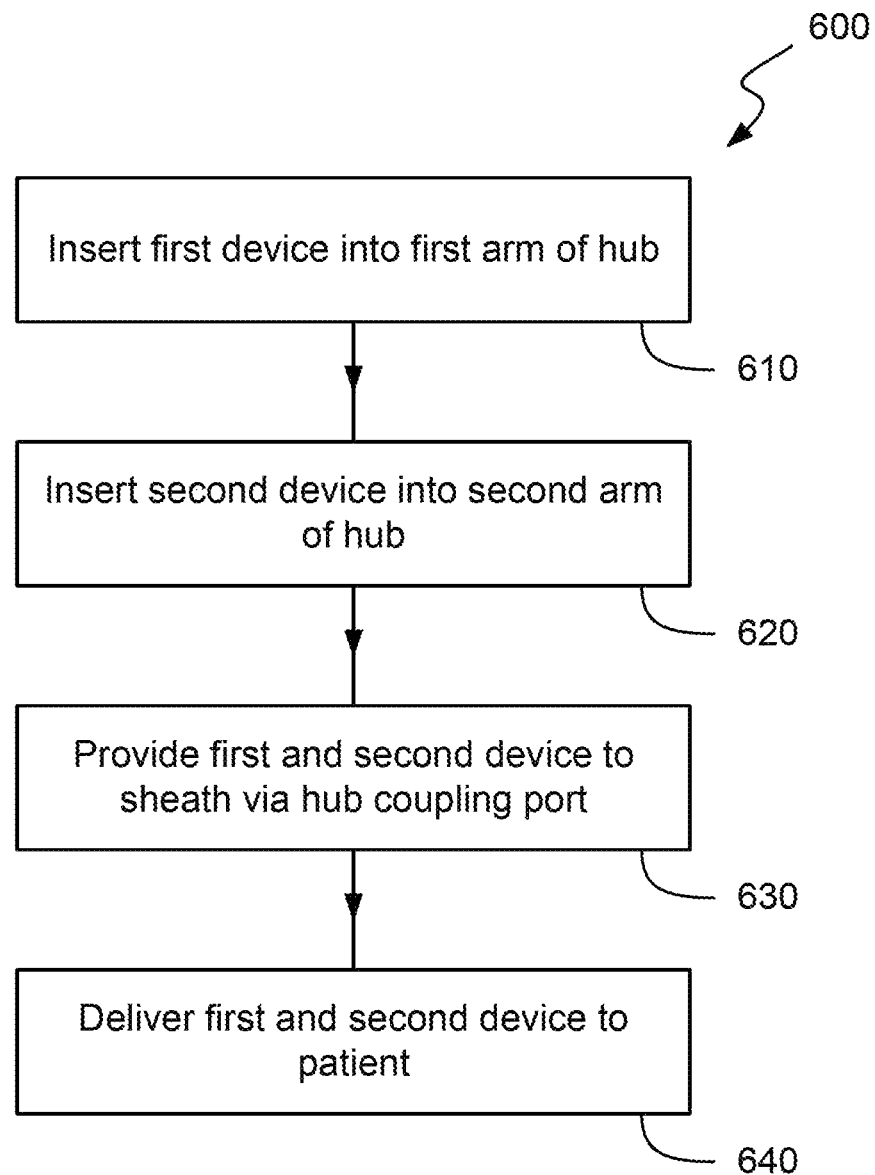
FIG. 6 shows an illustrative flowchart of a method of using a dual hub introducer sheath system according to aspects of the disclosure.

FIG. 6 illustrates an exemplary method 600 of using a dual hub introducer sheath, such as any of the introducer sheaths as described in the foregoing description, according to aspects of the technology. The method 600 will be described in relation to the exemplary systems depicted in FIGS. 1-5 above. Prior to using the dual hub introducer sheath, the sheath 210 is positioned into the arteriotomy of the patient (not indicated in FIG. 6). Prior to insertion of the sheath 210 into the patient, a connector port of the hub, such as connector port 270 of the hub 220 as described above, is coupled to a proximal end of an introducer sheath, such as end 212 of sheath 210 as described above. In some aspects of the technology, a dilator may be inserted into the lumen of the sheath before insertion into the patient, such as dilator 280 shown in FIGS. 2 and 3. The dilator assists with positioning the sheath in regions of the patient's body which are difficult to penetrate with the sheath alone. Once inserted, the dilator is removed from the lumen of the sheath.

In step 610, the first medical device 140 is inserted into a first arm 230 of the dual hub 220. Here, the first medical device 140 is pushed through the first hemostasis valve 238 and traverses the hub 220 towards the connector port 270. As with the first medical device 140, in step 620, the second medical device 160 is pushed through the second hemostasis valve 258 in the second arm 250, after which it also traverses hub 220 toward connector port 270. In step 630, the first and second medical devices are provided to the lumen of the sheath 210 via the connector port 270 of the hub 220. In step 640, the first and second medical devices are delivered into an arteriotomy of the patient by pushing the devices along the length of sheath 210 until they exit the distal end 214 of the sheath 210.

Figure 7:
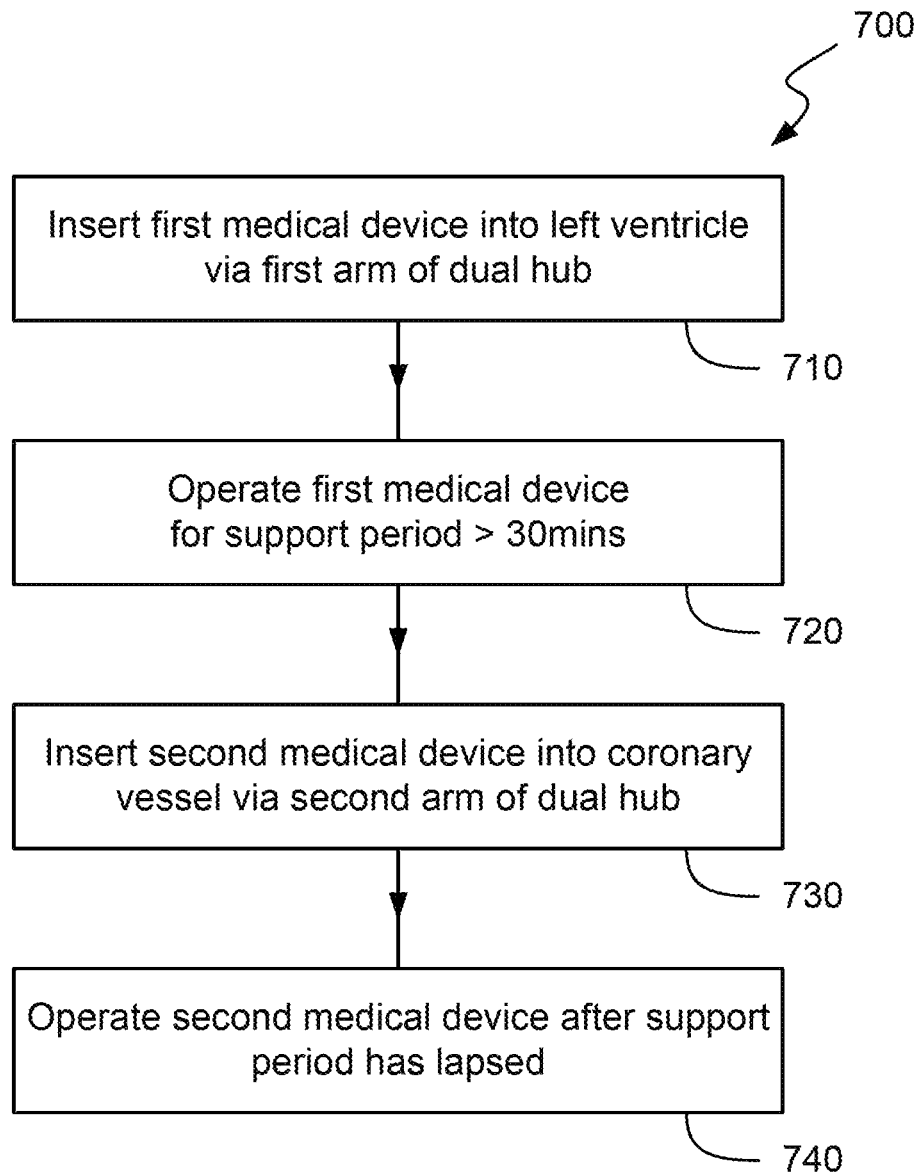
FIG. 7 shows an illustrative flowchart of a method of using a dual hub introducer sheath system for unloading the left ventricle of the heart according to aspects of the disclosure.

Once in position in the patient's arteriotomy, the medical devices can be used as desired to treat the patient. In some aspects of the technology, the dual hub introducer sheath may be used to unload the left ventricle of the patient, as shown in the exemplary method 700 of FIG. 7. In such cases, the first medical device 140 may be a mechanical circulatory support device, and the second medical device 160 may be a coronary reperfusion therapy device for providing the patient with percutaneous coronary intervention (PCI). With respect to FIG. 7, in step 710, after the first medical device 140 has emerged from the distal end 214 of the sheath 210, it is advanced into position in the left ventricle of the heart. The first medical device 140 may then be locked in position via a locking mechanism located on the first arm 230 of the hub 220. As already discussed, such locking mechanisms may include any one of: a Tuohy-Borst adaptor, an inflatable balloon, and a locking lever arm. In step 720, the mechanical circulatory device is operated within the left ventricle for a support period in excess of 30 minutes. In some aspects of the technology, the mechanical circulatory device may be operated at 2.5 L/min of blood flow. In step 730, the second medical device 160 is positioned into a coronary vessel of the patient. The second medical device 160 may then also be locked in position via a locking mechanism located on the second arm 250 of the hub 220 as previously discussed. In step 740, after the support period has passed, reperfusion therapy is applied to the coronary vessel via a PCI device, as described above. The reperfusion therapy may be performed in parallel with operation of the mechanical circulatory device, or after operation of the mechanical circulatory device.

In some aspects of the technology, the various steps discussed above with respect to methods 600 and 700 of FIGS. 6 and 7 may be performed in a different order and/or concurrently with each other. Furthermore, if desired, one or more of the above described steps may be optional or may be combined.

The foregoing description is merely intended to be illustrative of the principles of the technology. As such, the devices and methods described herein can be practiced by other than the described implementations, which are presented for purposes of illustration and not of limitation. It is to be understood that the systems, devices and methods disclosed herein, while described with respect to certain procedures, may be applied in any context where access to an arteriotomy of a patient is desired without creating multiple access sites in the vasculature of the patient. In addition, the disclosed features may be implemented in any combination or subcombination (including multiple dependent combinations and subcombinations) with one or more other features described herein. The various features described or illustrated above, including any components thereof, may also be combined or integrated into other systems. Finally, certain features may be omitted or not implemented without departing from the spirit of the technology.

The invention claimed is:

1. An introducer system comprising:
a hub configured to be coupled to a proximal end of an introducer sheath, the hub comprising:
a first arm having a first lumen and a first hemostasis valve, wherein the first lumen and the first hemostasis valve are configured to deploy a first medical device;
a second arm coupled to the first arm and having a second lumen and a second hemostasis valve, wherein the second lumen and the second hemostasis valve are configured to deploy a second medical device,
wherein the hub defines a distal opening configured to be coupled to the proximal end of the introducer sheath such that the first lumen and the second lumen are in communication with a lumen of the introducer sheath to allow the passage of at least one of the first medical device or the second medical device through the introducer sheath for delivery to a patient; and
a lever arm that is pivotable within the hub from an unlocked position to a locked position, wherein the lever arm comprises a notch configured to fit around and frictionally engage an external periphery of one of the first medical device and the second medical device when the lever arm is in the locked position.

2. The introducer system of claim 1, further comprising the introducer sheath.

3. The introducer system of claim 2, wherein the first arm is arranged parallel to a longitudinal axis of the introducer sheath.

4. The introducer system of claim 2, wherein the first arm and the second arm are arranged in a Y-shaped configuration with respect to the introducer sheath.

5. The introducer system of claim 2, wherein the introducer sheath is an expandable sheath.

6. The introducer system of claim 2, wherein the introducer sheath is a peel-away sheath.

7. The introducer system of claim 6, wherein the hub further comprises tabs to enable separation of the hub and the peel-away sheath.

8. The introducer system of claim 2, wherein the introducer sheath comprises at least one of: a polyether block amide; a polyethylene material; a polytetrafluoroethylene (PTFE) material; a high-density polyethylene (HDPE) material; a medium-density polyethylene (MDPE) material; or a low-density polyethylene (LDPE) material.

9. The introducer system of claim 1, wherein the hub further comprises at least one suture ring.

10. The introducer system of claim 1, wherein the first arm and the second arm each comprise at least one side-port.

11. The introducer system of claim 1, wherein at least one of the first arm or the second arm comprises an irrigation port configured to be supplied with an irrigation fluid.

12. The introducer system of claim 1, wherein, in the locked position, the lever arm is configured to prevent axial movement of the one of the first medical device and the second medical device within the introducer sheath after delivery to the patient.

13. The introducer system of claim 1, wherein the lever arm is biased in the locked position.

14. The introducer system of claim 1, wherein the hub comprises at least one of: ethylene-vinyl acetate (EVA); styrene-butadiene copolymer (SBC); styrene ethylene butylene styrene (SEBS); a high-density polyethylene (HDPE) material; a medium-density polyethylene (MDPE) material; a low-density polyethylene (LDPE) material; polyether ether ketone (PEEK); a polyether block amide; an elastomer; synthetic rubber; or a polyethylene, polyurethane, or polycarbonate material with an elastic modulus of about 40 ksi.

15. The introducer system of claim 1, wherein the second medical device is a coronary reperfusion therapy device for providing the patient with percutaneous coronary intervention (PCI).

16. The introducer system of claim 15, wherein the notch is configured to fit around and frictionally engage an external periphery of the coronary reperfusion therapy device when the lever arm is in the locked position.

17. The introducer system of claim 15, wherein the coronary reperfusion therapy device is a stent that is configured for insertion through the second arm and introducer sheath by a catheter.

18. The introducer system of claim 1, wherein the first medical device is a mechanical circulatory support device and comprises at least one of: a blood pump; a transvalvular axial-flow (TV)-pump; an intra-aortic balloon pump; or an extracorporeal membrane oxygenation (ECMO) pump.

19. The introducer system of claim 18, wherein the notch is configured to fit around and frictionally engage an external periphery of the mechanical circulatory support device when the lever arm is in the locked position.

20. The introducer system of claim 1, wherein the first medical device is a rotary blood pump having a cannula and a rotor and rotor housing.

21. The introducer system of claim 1, wherein the hub comprises a set of second arms comprising between two and five second arms, each given second arm of the set of second arms configured with a hemostasis valve and a lumen in communication with the introducer sheath for passage of the second medical device from the given second arm into the introducer sheath.

22. The introducer system of claim 21, wherein the set of second arms are arranged in a radially symmetric manner about the first arm.

23. The introducer system of claim 1, wherein the notch defines a space configured to receive the first medical device or the second medical device into the space when the lever arm is in the locked position.

24. The introducer system of claim 1, wherein the notch pinches the first medical device or the second medical device when the lever arm is in the locked position.

25. The introducer system of claim 1, wherein the notch bends the first medical device or the second medical device when the lever arm is in the locked position.

26. The introducer system of claim 1, wherein the lever arm has a first end that is pivotably connected to the hub.

27. The introducer system of claim 26, wherein the lever arm has a second end comprising a surface and a recess in the surface, wherein, when the lever arm is in the locked position, the recess engages a protrusion located within the hub to secure the lever arm in the locked position.

* * * * *

UNITED STATES PATENT AND TRADEMARK OFFICE
CERTIFICATE OF CORRECTION

| | | |
|---|---|---|
| PATENT NO. | : 12,350,445 B2 | Page 1 of 1 |
| APPLICATION NO. | : 16/815690 | |
| DATED | : July 8, 2025 | |
| INVENTOR(S) | : Glen R. Fantuzzi | |

It is certified that error appears in the above-identified patent and that said Letters Patent is hereby corrected as shown below:

In the Specification

In the Background
Column 1, Line 17:
Now reads: "Impella2.5®"; should read -- Impella 2.5® --

In the Background
Column 1, Line 17:
Now reads: "Impella5.0®"; should read -- Impella 5.0® --

In the Brief Summary
Column 5, Line 25:
Now reads: "(HDPE)"; should read -- (MDPE) --

Signed and Sealed this
Twenty-third Day of September, 2025

John A. Squires
*Director of the United States Patent and Trademark Office*